(12) United States Patent
Miao et al.

(10) Patent No.: US 11,426,294 B2
(45) Date of Patent: Aug. 30, 2022

(54) DEGRADABLE FOLDABLE BIOLOGICAL AMNIOTIC MEMBRANE COMPOSITE REPAIR STENT

(71) Applicant: JIANGXI RUIJI BIOTECHNOLOGY CO., LTD, Jiangxi (CN)

(72) Inventors: Chunyun Miao, Jiangxi (CN); Hu Lv, Jiangxi (CN); Chongjun Peng, Jiangxi (CN); Zhiqiang Teng, Jiangxi (CN)

(73) Assignee: JIANGXI RUIJI BIOTECHNOLOGY CO., LTD, Jiangxi (CN)

( * ) Notice: Subject to any disclaimer, the term of this patent is extended or adjusted under 35 U.S.C. 154(b) by 0 days.

(21) Appl. No.: 17/043,876

(22) PCT Filed: Dec. 17, 2018

(86) PCT No.: PCT/CN2018/121627
§ 371 (c)(1),
(2) Date: Sep. 30, 2020

(87) PCT Pub. No.: WO2020/052136
PCT Pub. Date: Mar. 19, 2020

(65) Prior Publication Data
US 2021/0030571 A1     Feb. 4, 2021

(30) Foreign Application Priority Data
Sep. 14, 2018   (CN) .......................... 201811076735.7

(51) Int. Cl.
*A61F 2/90* (2013.01)
(52) U.S. Cl.
CPC .......... *A61F 2/90* (2013.01); *A61F 2240/002* (2013.01); *A61F 2250/0018* (2013.01); *A61F 2250/0023* (2013.01)

(58) Field of Classification Search
CPC ...... A61F 2/04; A61F 2/06; A61F 2/07; A61F 2/82; A61F 2/90; A61F 2240/002; A61F 2250/0018; A61F 2250/0023
See application file for complete search history.

(56) References Cited

U.S. PATENT DOCUMENTS

2005/0147644 A1    7/2005  Sahota
2010/0228335 A1*   9/2010  Schorgl ................... A61L 31/08
                                                       623/1.15

FOREIGN PATENT DOCUMENTS

CN         2394603 Y       9/2000
CN       201005859 Y       1/2008
(Continued)

OTHER PUBLICATIONS

Corresponding International Patent Application No. PCT/CN2018/121627, International Search Report dated Jun. 10, 2019. English Translation.
(Continued)

*Primary Examiner* — Dinah Baria

(57) ABSTRACT

The present invention discloses a degradable foldable biological amniotic membrane composite repair stent, comprising a tubular body with an axially extending through hole, the front end of the tubular body is provided with an elastic balloon, and the end of the tubular body is connected to a one-way valve which seals the through hole here, the outer face of the elastic balloon is coated with a foldable reticulated polylactic acid stent, the outer surface of the foldable reticulated polylactic acid stent is coated with a biological amniotic membrane, and there are a plurality of micropores on meshes of the foldable reticulated polylactic acid stent, the plurality of micropores are filled with biological amniotic membrane powder; in the initial state, the elastic balloon, the foldable reticulated polylactic acid stent, and the biological amniotic membrane are compressed into a tight (Continued)

state; in the use state, after being implanted in the body and expanded under pressure, it can conform to the lacrimal duct/uterine cavity to form a tubular or drop-like shape or other spatial shape that adapts to the body cavity.

6 Claims, 1 Drawing Sheet

(56) References Cited

FOREIGN PATENT DOCUMENTS

| | | |
|---|---|---|
| CN | 102120059 A | 7/2011 |
| CN | 202184823 U | 4/2012 |
| CN | 102657913 A | 9/2012 |
| CN | 103349798 A | 10/2013 |
| CN | 204192801 U | 3/2015 |
| CN | 107647952 A | 2/2018 |
| CN | 107744417 A | 3/2018 |
| CN | 108042248 A | 5/2018 |
| WO | WO-2016176444 A1 * 11/2016 ............. B29C 41/00 |

OTHER PUBLICATIONS

Corresponding International Patent Application No. PCT/CN2018/121627, Written Opinion of the International Searching Authority dated Jun. 10, 2019.

* cited by examiner

DEGRADABLE FOLDABLE BIOLOGICAL AMNIOTIC MEMBRANE COMPOSITE REPAIR STENT

FIELD OF THE INVENTION

The present invention generally relates to the biomedical technology, and more particularly to a multi-purpose degradable foldable biological amniotic membrane composite repair stent.

BACKGROUND OF THE INVENTION

Lacrimal duct obstruction diseases (LDOD) are a class of diseases with lacrimal duct obstruction (striction or/and occlusion of the lacrimal duct) as pathological features and epiphora as main clinical manifestation. According to incomplete statistics, LDOD accounts for about 3% of outpatients in ophthalmology clinics, and it is a common and frequently-occurring disease in ophthalmology. Lacrimal duct obstruction may occur in any part of the lacrimal duct. The obstruction of lacrimal canaliculus is a common type of LDOD, and its incidence accounts for about 16% to 25% of LDOD. The obstruction of lacrimal canaliculus may be caused by a number of factors, including inflammation, trauma, congenital abnormalities, drugs, systemic diseases, iatrogenic injury, degeneration, etc.

The treatments for obstruction of lacrimal canaliculus mainly include non-surgical treatment and surgery combined catheterization.

Non-surgical treatment methods mainly include lacrimal laser, punctum dilation, probing of lacrimal passage, irrigation of lacrimal passage, etc. The laser endolacrimal recanalisation adopts the thermal effect of laser and its blasting effect to carbonize the blocked part. It is suitable for cases with short course of disease and small obstruction range, without lacrimal sac dilation or atrophy. Although non-surgical treatments such as punctum dilation, probing of lacrimal passage, and irrigation of lacrimal passage are simple, improper operation can easily cause iatrogenic injuries such as punctum dilation, lacrimal mucosa injury, and false duct formation. The above four treatment methods dredge the lacrimal passage by mechanical dilation or burning of the blocked part of the inner wall of lacrimal passage. However, the mucosal wall of the lacrimal passage after dredging may form an inner wall wound due to mechanical expansion or thermal burning, and the mucosal layer has not been completely epithelialized. At this time, if there is no support for the lacrimal duct wall, the lacrimal duct lumen is closed. With the healing of the lacrimal canaliculus injury, adhesions will occur at the wound site or the lacrimal duct wall scars and shrinks to cause secondary obstruction.

In order to improve the long-term postoperative effect of obstruction of lacrimal canaliculus, combined therapy is usually used after lacrimal canaliculus probing or laser plasty to reduce the recurrence rate of obstruction of lacrimal canaliculus after dredging, that is, placing proper lacrimal duct support in the lumen of the lacrimal canaliculus after dredging, which can mechanically expand and isolate the wound caused by probing, thereby preventing the adhesion of the wound. The existing methods to reduce the re-obstruction after lacrimal canaliculus catheterization are to implant various types of lacrimal duct stents or lacrimal duct rods in the lacrimal duct (operation combined with catheterization), such as lacrimal canalicular laser dredging combined with catheterization, lacrimal canaliculus catheterization combined with 0.02% MMC (mitomycin C) eye drops, lacrimal canaliculus incision combined with catheterization, and surgery combined with drug therapy. These methods have improved the long-term surgical effect of obstruction of lacrimal canaliculus, but there is still re-obstruction of lacrimal canaliculus after dredging, and various complications caused by catheter placement are still not resolved effectively (formation of wounds in the mucous membrane of the lacrimal canaliculus wall and the occurrence of traumatic inflammation and edema after dredging the lacrimal canaliculus part; the mucosal inner walls that are not completely repaired adhere to each other and the formation of scar contraction during the damage repair process causes re-obstruction after operation; adhesion of implanted canaliculus and cavity wall, and new trauma caused by extubation, re-obstruction of lumen of the lacrimal duct caused by wound re-adhesion), so re-obstruction or stenosis is prone to occur after the operation.

The support uses different materials, including silk thread, gut, polyethylene plastic catheter, metal tube, rubber tube, etc. The most widely used material at present is silicone tube. There are many types of lacrimal silicone stents, mainly including Crawford tube, self-retaining stent (SRS), dual-way silicone catheter, etc. The lacrimal silicone tube has super elasticity and toughness, and can become a thin strip without breaking under strong pulling, etc. Silicone tube catheterization can bring many disadvantages. As foreign bodies, it can cause irritation to the skin, eye conjunctiva and lacrimal mucosa. In severe cases, it may even cause rejection and reduce patient compliance. During the operation of inserting the silicone tube, it is easy to form false channel or cause punctum splitting or tearing of the lacrimal canaliculus, resulting in unsmooth irrigation of lacrimal passage and failure of the operation. The silicone tube is flexible and has poor conformability, and if it is not fixed properly after implanting lacrimal passage, it may cause spondylolisthesis; long-lasting expansion and compression of the tube wall is not only not conducive to the fading of inflammation and edema of the inner wall and the repair of the tube wall mucosa, but also can cause chronic inflammation of the lacrimal duct wall. In severe cases, the silicone tube stimulates the lacrimal mucosa to form granulation tissues and wrap the silicone tube, which makes it difficult to extubate. The long-term indwelling of the silicone tube can easily cause eyelid ectropion, which affects the appearance of the eyelids and the siphon and tear guiding functions of the lacrimal duct.

The Chinese patent numbered 99246881.7 discloses a lacrimal passage probing device with metal probes at both ends and a soft silicone tube in the middle. The metal probe is a small smooth stainless steel tube composed of a head end and a long handle. The implantation of the silicone tube stent can support the stoma, and drain exudation and secretions in the lacrimal sac, reduce inflammation, and accelerate the healing of the wound. However, clinical practices have found that the silicone tube stent may cause injury to the lacrimal duct tissues due to friction during pulling. When indwelling, adhesion with the lacrimal duct wall may occur, and when extubating, secondary injury occurs, causing re-obstruction of lacrimal passage, etc.

The Chinese patent numbered 200720005808.4 discloses a lacrimal duct probing drainage tube. This design enables the product to support the lacrimal duct tube, with the functions of flushing and drug delivery. However, the product has no repair function, and the tube body needs to be pulled out, which is easy to cause secondary damage.

The Chinese patent numbered 2017110803382 discloses an amniotic membrane lacrimal duct repair stent. It adopts an amniotic membrane stent body made of freeze-dried amniotic membrane. The sheet-shaped amniotic membrane is made into a tube, rod or strip shape by twisting, and there is a medical suture thread respectively connected to the two ends of the amniotic membrane stent body, and the length of the amniotic membrane stent body between the two suture nodes is slightly larger than that of the medical suture between the two suture nodes. The amniotic membrane lacrimal duct repair stent is simple and time-saving to operate, easy to adapt to the tortuous structure of the lacrimal duct, which can avoid damage to the lacrimal duct tissue due to pulling friction and secondary obstruction caused by adhesions, and at the same time, it has good therapeutic effect on the diseased tissue. It is conducive to the recovery of lacrimal epithelial function and prevents scar formation. The amniotic membrane can be made of degradable material without extubation, with good long-term effect and low recurrence rate. Since the amniotic membrane stent body has a constant diameter along its length, it is necessary to make the products of various specifications according to the sites of use.

Intrauterine adhesions (IUA), also known as Asherman syndrome, refer to intrauterine muscle wall and/or cervical tube adhesion after injury of uterine cavity or cervical tube basement membrane caused by various factors. It can affect the menstruation and fertility functions of women at the childbearing age. During pregnancy and non-pregnancy, the intrauterine trauma, infection, uterine malformations, and genetic tendencies are the main reasons for the formation of IUA. The main histopathological changes of IUA are endometrial fibrosis and scar formation. Clinically, IUA is mostly manifested as amenorrhea or reduced menstrual flow, periodic abdominal pain, infertility, placental implantation after pregnancy, fetal growth restriction, postpartum hemorrhage, etc., seriously affecting the reproductive health of women of childbearing age.

Trans-cervical resecdon of adhesions (TCRA) is the standard surgical procedure for IUA. However, for patients with severe IUA, the basement membrane of the endometrium almost has no regenerative functions after severe damage. It is difficult for intimal regeneration after electrosurgical separation in TCRA; in addition, with the presence of electrothermal effect during surgical resection and electrocoagulation to stop bleeding, the tissue wounds damaged by heat undergo pathological repair and form inflammatory granulation tissues and fibrous scars, which causes the re-adhesion of anterior and posterior walls of the uterine cavity that is not covered. Effectively promoting the repair of the basement membrane of the endometrium is a key and difficulty to prevent the formation of re-adhesion and treat IUA.

There are the following methods to prevent t re-adhesion after IUA. Firstly, barrier medium method, including the use of intrauterine device and Foley balloon catheter. The intrauterine device cannot effectively separate the anterior and posterior walls of the uterus and may cause excessive inflammation, leading to a large number of inflammatory mediators, promoting the release of adhesion-forming cytokines, and accelerating the formation of postoperative re-adhesion. During Foley balloon urethral treatment, patients need to be hospitalized, with the possibility of secondary infections or even cervical insufficiency; when the intrauterine balloon is compressed, the endometrium is difficult to grow; this method has a short treatment period, and its long-term effect on preventing re-adhesion has not been confirmed. Secondly, medicinal treatment. Estrogen and progesterone are routinely given for a sequential artificial cycle of 2 to 3 months after IUA separation, or estrogen alone is used. The above measures are effective in preventing the formation of re-adhesion after adhesion separation in patients with mild to moderate IUA. The menstrual recovery and reproductive prognosis are significantly improved. However, its effect on severe IUA patients is not optimistic, and the post-operative re-adhesion rate is more than 50%. In recent years, studies have shown that, when there is no difference in serum estrogen levels in IUA patients, the estrogen receptor (ER) and transforming growth factor $\beta 1$ (TGF-$\beta 1$) on the surface of adhesion tissues are significantly increased, and local high estrogen level may increase the level of pro-fibrotic cytokines by prompting TGF-$\beta 1$ and participate in the occurrence of adhesion. The study suggests that in patients with severe IUA, their intimas and basement membranes are severely damaged, and in case of lack of response to estrogen, it blindly focuses on whether high estrogen levels will increase the level of some adhesion-promoting factors, aggravate re-adhesion and cause the occurrence of intimal fibrosis. Therefore, the functions of estrogens in the formation of re-adhesion after adhesion separation in severe IUA need to be further explored. Thirdly, amniotic membrane transplantation. After TCRA, the ideal subsequent treatment is to adopt a biologically active mechanical barrier to inhibit intrauterine re-adhesion and promote epithelial regenerative repair. Human fetal amniotic membrane is a natural polymer biomaterial. It is the most active part of the placenta for cell growth and differentiation, and contains a plurality of components such as collagen, glycoproteins, proteoglycans, integrins and lamellar bodies, etc. It can express a variety of growth factors and their mRNA-related proteins, to provide rich nutrients for cell proliferation and differentiation. Transplanting amniotic membrane into the uterine cavity can provide a good biological barrier, and inhibit the inflammation response, promote the intrauterine membrane repair and growth. At present, there is no better material than amniotic membrane in terms of promoting repair. Intrauterine amniotic membrane implantation and the application of amniotic membrane tissue engineering materials will become a new method for the treatment of IUA.

The Chinese patent numbered 201110058056.9 discloses a drug-coated stent for preventing and treating IUA. The stent is woven into a uterine-shaped mesh basket with nickel-titanium alloy wire, and the mesh basket is coated with a biocompatible membrane, and the membrane is sprayed with a sustained release drug-loaded coating, and the drugs are estrogen and progesterone. The stent described in the patent is made of non-degradable materials, and it is not described how to take out the stent after being delivered into the uterine cavity. It is easy to find that the stent is difficult to take out and may even cause secondary trauma.

Amer et al. (2006) made attempt to perform intrauterine amniotic membrane transplantation using Foley balloon catheter as a support after TCRA in 25 patients with moderate to severe IUA. It aimed to replace the endometrial basement membrane with regenerative amniotic membrane epithelium, to prevent formation of re-adhesion after TCRA, promote the recovery of menstruation and fertility, and certain clinical effect has been achieved. However, the balloon is spherically enlarged in the uterine cavity. The swelling is inconsistent with the shape of the uterine cavity, with only a part of the balloon is in contact with the cavity wall; in addition, the amniotic membrane is blindly placed in the uterine cavity. When it is placed, the amniotic membrane is too thin, it will stick together and cannot be deployed and attached to the inner wall of the uterine cavity as expected, leading in inconvenient operation, and the amniotic membrane cannot play its role.

Duan Hua et al. filed a patent application for "a carrier barrier system for the prevention and treatment of IUA" (CN 102657913A). In the application, amniotic membrane cells rather than complete amniotic membrane are injected into uterine cavity as a kind of carrier barrier material that can be added. Therefore, the materials have no unique biological functions of a complete amniotic membrane. Because this technology is to modify the amniotic membrane, and the cells are taken, the modified amniotic membrane tissue structure has undergone a fundamental change, without the original regeneration and repair functions any longer. A large number of studies have shown that the amniotic basement membrane and amniotic membrane matrix layer contain a large number of different collagens, mainly type I, III, IV, V, VII collagens and fibronectin, laminin, etc. These components enable the amniotic membrane to act as a "transplanted basement membrane", to play the role of a new healthy and suitable matrix to promote epithelialization. Tseng believed that the thick basement membrane and avascular matrix of the human amniotic membrane are the keys to the success of the transplantation. The patent has no ideal regeneration and repair functions due to the destruction of amniotic membrane tissue structure. In addition, as the injected barrier materials fill the uterine cavity and are blocked by a sphere, the uterine cavity has poor air permeability, which may affect the normal skin respiration, metabolism and wound repair.

Thus, it is an urgent issue to be solved to easily transplant the amniotic membrane with regenerative repair functions into the uterine cavity after TCRA operation, to expand and attach it, and when the amniotic membrane support is taken out, the amniotic membrane will not be brought out, and there will be no damage to new wounds or cervix, etc.

In summary, for the treatment of lacrimal duct obstruction, IUA and related diseases, there exist the following common problems: firstly, after the non-surgical dredging of lacrimal duct obstruction or IUA resection, there is no support for lacrimal duct wall/uterine cavity wall, the lacrimal duct cavity/uterine cavity wall is closed. During the healing process, the wounds will undergo pathological repair, and granulation tissue or the scar of lacrimal duct/uterine cavity wall will form to cause adhesion; secondly, the non-degradable material stent, as a foreign body, stimulates the lacrimal duct/uterine mucosa, and even causes rejection reactions in severe cases; thirdly, improper fixation of the stent after implanted into lacrimal duct/uterine cavity causes spondylolisthesis; fourthly, the implantation of the stent produces long-lasting dilation and compression on the tube wall, which is not conducive to the fading of inflammation and edema of the inner wall and the repair of the mucosa of the tube wall, hinders the normal tissue repair. It can cause chronic inflammation of the canaliculus tube wall/uterine cavity wall. In severe cases, it can stimulate the mucosa to form granulation tissue and wrap the implanted stent, leading to difficulty in removing the stent and even causing secondary trauma; fifthly, the stent expansion is inconsistent with the shape of lacrimal duct/intrauterine space, and the stent is only partially in contact with the cavity wall, which is not conducive to the entry of biologically active substances or drugs into the tissues to play their roles.

SUMMARY OF THE INVENTION

In order to solve the foregoing problems in the prior art, the present invention provides a degradable foldable biological amniotic membrane composite repair stent.

The present invention is achieved through the following technical solutions:

A degradable foldable biological amniotic membrane composite repair stent, comprising a tubular body with an axially extending through hole, the front end of the tubular body is provided with an elastic balloon, and the end of the tubular body is connected to a one-way valve which seals the through hole here, the elastic balloon is arranged in the lumen of a foldable reticulated polylactic acid stent, the outer surface of the foldable reticulated polylactic acid stent is coated with a biological amniotic membrane, and there are a plurality of micropores on meshes of the foldable reticulated polylactic acid stent, the plurality of micropores are filled with biological amniotic membranes; in the initial state, the elastic balloon, the foldable reticulated polylactic acid stent, and the biological amniotic membrane are compressed into a tight state; in the use state, the elastic balloon is injected with sterile gas or liquid to expand to adapt to the shape of the body cavity of the affected area (tube, water drop-like shape, or other body cavity shape), and stretch out the foldable reticulated polylactic acid stent and attach to the inner wall of the affected area, and then the sterile gas or liquid is drawn out, and when the elastic balloon is shrunk, the tubular body is withdrawn.

Preferably, the foldable reticulated polylactic acid stent is woven from filamentous polylactic acid.

Preferably, the foldable reticulated polylactic acid stent is made of polylactic acid material by laser engraving.

Preferably, the foldable reticulated polylactic acid stent is made of polylactic acid material by 3D printing.

The invention further provides an alternative technical solution:

A degradable foldable biological amniotic membrane composite repair stent, comprising a tubular body with an axially extending through hole, the front end of the tubular body is provided with an elastic balloon, and the end of the tubular body is connected to a one-way valve which seals the through hole here, sheet-like polylactic acid and sheet-like amniotic membrane are laminated and wound on the outer surface of the elastic balloon, there are a plurality of micropores on the sheet-like polylactic acid and the plurality of micropores are filled with biological amniotic membranes; in the initial state, the elastic balloon, the sheet-like polylactic acid, and the sheet-like amniotic membrane are compressed into a tight state; in the use state, the elastic balloon is injected with sterile gas or liquid to expand to adapt to the shape of the body cavity of the affected area (tube, water drop-like shape, or other body cavity shape), and stretch out the sheet-like polylactic acid and the sheet-like amniotic membrane and attach to the inner wall of the affected area, and then the sterile gas or liquid is drawn out, and when the elastic balloon is shrunk, the tubular body is withdrawn.

Preferably, the sheet-like polylactic acid has a limit position after being stretched by the elastic balloon, and the sheet-like polylactic acid is provided with a locking mechanism to maintain the limit position.

Preferably, the sheet-like polylactic acid is a polylactic acid sheet with meshes.

Compared with the prior art, the present invention has the following beneficial effects: the foldable reticulated polylactic acid stent coated with biological amniotic membrane has better fit to the lacrimal duct wall or intrauterine wall after stretching, so that the biological functions of amniotic membrane such as promoting repair, reducing scar formation, reducing inflammation, and preventing adhesion, can be fully exerted. The foldable reticulated polylactic acid stent has good strength and hardness. After being stretched, it can maintain its shape and can be stably supported in the lacrimal passage or uterine cavity, without blocking the lacrimal passage or uterine cavity, thereby maintaining the lacrimal passage or uterine cavity unblocked, with better drainage effect. The degradation time of foldable reticulated polylactic acid stent is selective, which can meet clinical needs. After the biological amniotic membrane coated on the outer surface of foldable reticulated polylactic acid stent is completely degraded, while the foldable reticulated polylactic acid stent is being degraded, the amniotic membrane powder filled in the micropore of the reticulated polylactic acid stent can continue to slowly play the repair role of amniotic membrane, and continue to maintain the biological activity of the amniotic membrane until the wound is completely healed.

The structure of amniotic membrane is mainly composed of basement membrane layer and amniotic membrane stem cells (the epithelial cell layer is attached to the surface of the basement membrane, and the mesenchymal stem cells are scattered in the reticular structure of the basement membrane). They have elasticity and have a thickness of 0.02-0.5 mm. Amniotic membrane cells can secrete a large amount of biologically active substances to promote and regulate tissue growth and development. More than 150 kinds of cell growth regulators and a variety of active proteases are detected in the amniotic membrane, and they form a complex network-like regulatory mechanism that works together to regulate cell growth, differentiation and activity, and can regulate the cytokine expression and secretion of local tissues in different time phases, and promote the repair and healing of injured tissues. The matrix layer collagen fibers (types I, III, IV, V, VII collagens) that make up the basement membrane of the amniotic membrane are interwoven into a network, with a mesh gap of about 0.5~1.5 μm; there are a large amount of fibronectins and laminin filled in the mesh gap that tightly combined with collagen fibers through hydrogen bonding, metal chelation, electrostatic attraction, etc., so that the collagen fiber network has better elasticity and toughness; and through these mechanisms, a large number of biologically active factors secreted by amniotic membrane stem cells are fixed in the basement membrane network structure to continue to play their biological roles. The special biomechanical structure is conducive to cell attachment, growth and prolongation, so that the amniotic membrane can act as a "transplanted basement membrane" and exert the functions of a new healthy and suitable matrix, to promote cell growth.

Through a large number of studies, the amniotic membrane has been found to have the effect of promoting tissue wound repair, inhibiting local inflammation, mechanical isolation and preventing adhesion of injured wounds, reducing and inhibiting scar formation, etc. because of the following: ① the complete structure of amniotic membrane basement membrane matrix is the key that determines its role in promoting tissue repair; ② A large number of cytoactive factors are an indispensable factor for amniotic membrane to exert its functions; ③ The time limit for maintaining a complete structure in the body is consistent with the tissue repair process (that is, to maintain a good separation effect during the period of inflammatory hyperplasia within 1 to 3 months (the tissue is prone to adhesion)); ④ The amniotic membrane stent body must be compatible with the implanted body cavity characteristics, and the amniotic membrane maintains a good attachment state to the tissue wound; ⑤ The stent system has good semi-permeability, allowing gas and small molecular substances to pass through, to facilitate tissue respiration and discharge of metabolites.

Based on the above research results and the problems in the prior art, the tubular body of the present invention includes two parts: a foldable reticulated polylactic acid stent and a complete amniotic membrane wrapped in an outer layer. According to the treatment needs of different diseases, by adjusting the polymerization temperature, time, polymer molecular weight, glycolic acid addition and other key process factors during the polymerization process, the degradation time, compliance, support strength characteristics, and integrity of the polylactic acid material stent, the stent can be adjusted within 3 to 6 months, to meet the needs. Through laser engraving, etc., it is processed into a large number of nano-scale micropore fibers, and the polylactic acid tube maintains good semi-permeability. However, the pure polylactic acid material does not have the biological activity of promoting tissue repair, with poor effect. After the amniotic membrane is pulverized into a powder, its particles form a microvilli globular structure, which contains a skeleton system composed of collagen fibers, and a large amount of fibrin and laminin are attached between the puff fibers. These proteins have high levels of adhesion and firmly fix small molecule cytokines in spherical amniotic membrane powder. However, it is difficult to effectively repair the wound surface due to the destruction of the integral structure of the basement membrane. In the present invention, the amniotic membrane powder is filled in the meshes of the polylactic acid tube through mechanical pressure to form a composite membrane. When the composite membrane is not in use, the end fibers of the amniotic membrane powder balls and the polylactic acid tube network structure are entangled and firmly bonded; after implantation in the body, with the high adhesion of fibrin and laminin in the environment of body fluids, it can be integrated with polylactic acid tube stent through a variety of bonding effects, to make it possess complete network structure and biological activities of amniotic membrane. However, since the active substance contained is lower than the complete amniotic membrane, its tissue repair effect is weaker than that of the complete amniotic membrane. In order to solve this problem, in the present invention, a layer of complete amniotic membrane (in vivo degradation time is about 3 months) is wrapped on the outer surface of the foldable reticulated polylactic acid stent. The composite structure tubular stent is delivered into the body through the delivery system. Because the tubular body of the stent has good elasticity and rigidity, the stent is very stable and will not slip off after implanted in the body, and will closely attach to the inner surface of the body cavity. According to the characteristics of the in vivo wound recovery process, it is an acute inflammatory recovery process within 3 months. The inflammatory cells infiltrate the damaged wound surface, causing massive proliferation of granulation tissues and scarring. If there is no stent support, adhesions are likely to occur; after 3 months, the inflammation is gradually reduced, and the proliferation of granulation tissues is reduced until the tissue is completely repaired. At this stage, stent support and isolation is required, otherwise tissue adhesions may occur in some patients. Within 3 months after implantation of the stent, the intact amniotic membrane mainly plays the role of promoting repair, and 3 months later, the amniotic membrane powders in the micropore of the mesh polylactic acid stent continue to slowly play its role of repairing, and continue to maintain its biologically active functions until the wound is completely healed.

In summary, the present invention solves the following key problems in the treatment of lacrimal duct obstruction/IUA: ① a tubular body of degradable foldable biological amniotic membrane composite repair stent is implanted in the lacrimal duct/intrauterine cavity, which supports the lacrimal duct wall/intrauterine wall, effectively prevents the closure of lacrimal duct cavity/intrauterine wall, and avoids the formation of granulation tissues and tissue adhesion caused by scarring and contraction of the lacrimal duct/intrauterine wall in the later stage of wound healing; ② The tubular body of the stent is made of a biodegradable material, with good biological compatibility, and it has no irritation to the lacrimal duct/uterine mucosa and will not cause rejection reactions; ③ The tubular body of the stent has good elasticity and rigidity, the stent is very stable and will not slip off after implanted in the body; ④ The implanted stent will be gradually degrade as the tissue is repaired, and the dilation and compression of the tube wall will adapt to the tissue repair process, and the stent completely retains a variety of biological activities of amniotic membrane itself of promoting tissue repair, resisting inflammation, downregulating the level of tissue TGF-β1, resisting fibrosis and inhibiting scar formation, etc., which is conducive to alleviating the inflammation of the inner wall and promoting the repair of tubular wall/cavity wall mucosa. ⑤ The degradation time of the tubular body of the degradable stent is controllable, and it is completely degraded as the tissue repair is completed, without the need to remove the stent, which avoids the secondary trauma caused by the removal of the stent; ⑥ The composite tubular body has good elasticity and rigidity that can be adjusted as needed, and the pressure balloon can be expanded into different shapes as required. The stent completely adapts to the shape of the lacrimal duct/intrauterine space after expansion and is in full contact with the cavity wall, which is conducive to the entry of biologically active substances or drugs into the tissues to play their roles.

DETAILED DESCRIPTION OF THE EMBODIMENTS

Figure 1:
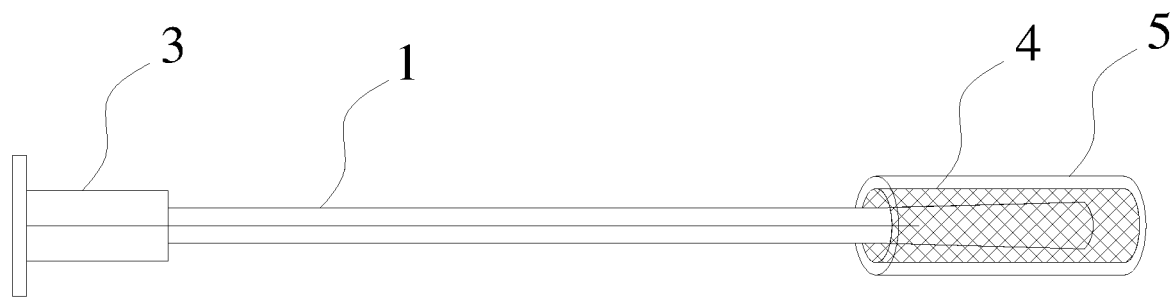
FIG. 1 is a structural schematic diagram of a degradable foldable biological amniotic membrane composite repair stent in the initial state of the present invention.
Figure 2:
FIG. 2 is a structural schematic diagram of a degradable foldable biological amniotic membrane composite repair stent in use state of the present invention.
Figure 3:
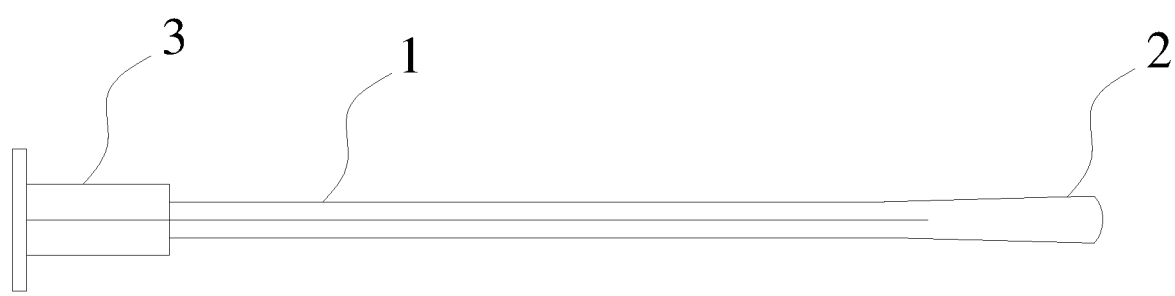
FIG. 3 is a structural schematic diagram of a tubular body of the present invention that is withdrawn after implanting a degradable foldable biological amniotic membrane composite repair stent into the affected area.

The degradable foldable biological amniotic membrane composite repair stent of the present invention is further described in conjunction with specific embodiments in details below.

EXAMPLE 1

A degradable foldable biological amniotic membrane composite repair stent, comprising a tubular body 1 with an axially extending through hole, the front end of the tubular body 1 is provided with an elastic balloon 2, and the end of the tubular body 1 is connected to a one-way valve 3 which seals the through hole here, the elastic balloon 2 is arranged in the lumen of a foldable reticulated polylactic acid stent 4, the foldable reticulated polylactic acid stent 4 is made of polylactic acid material by laser engraving, the outer surface of the foldable reticulated polylactic acid stent 4 is coated with a biological amniotic membrane 5, and there are a plurality of micropores on meshes of the foldable reticulated polylactic acid stent 4, the plurality of micropores are filled with biological amniotic membrane powder; in the initial state, the elastic balloon 2, the foldable reticulated polylactic acid stent 4, and the biological amniotic membrane 5 are compressed into a tight state; in the use state, the elastic balloon 2 is injected with liquid to expand to adapt to the shape of the affected area, and stretch out the foldable reticulated polylactic acid stent 4 and attach to the inner wall of the affected area, and then the liquid is drawn out, and when the elastic balloon 2 is shrunk, the tubular body 1 is withdrawn.

The degradable foldable biological amniotic membrane composite repair stent is made by the following method: a foldable reticulated polylactic acid stent 4 with a plurality of micropores is made by degradable polylactic acid material through laser engraving, and the foldable reticulated polylactic acid stent 4 is uniformly sprayed with biological amniotic membrane powder on the surface, and the elastic balloon 2 is placed in the lumen of the foldable reticulated polylactic acid stent 4, and then sheet-shaped biological amniotic membrane 5 is wrapped on the outer surface of the foldable reticulated polylactic acid stent 4. The biological amniotic membrane 5 can be fixed with the foldable reticulated polylactic acid stent 4 with medical adhesive, and then put into a squeeze machine for compression. The compression process includes two stages. In the first stage, adjust the pressure of the squeeze machine to 0.2 MPa and hold 30 min, and in the second stage, adjust the squeeze machine to 0.5 MPa and hold 10 min; after compression, package and sterilize to obtain a degradable foldable biological amniotic membrane composite repair stent.

EXAMPLE 2

A degradable foldable biological amniotic membrane composite repair stent, comprising a tubular body 1 with an axially extending through hole, the front end of the tubular body 1 is provided with an elastic balloon 2, and the end of the tubular body 1 is connected to a one-way valve 3 which seals the through hole here, the elastic balloon 2 is arranged in the lumen of a foldable reticulated polylactic acid stent 4, the foldable reticulated polylactic acid stent 4 is woven from filamentous polylactic acid, the outer surface of the foldable reticulated polylactic acid stent 4 is coated with a biological amniotic membrane 5, and there are a plurality of micropores on meshes of the foldable reticulated polylactic acid stent 4, the plurality of micropores are filled with compound amniotic membrane gel; in the initial state, the elastic balloon 2, the foldable reticulated polylactic acid stent 4, and the biological amniotic membrane 5 are compressed into a tight state; in the use state, the elastic balloon 2 is injected with sterile gas or liquid to expand to adapt to the shape of the affected area, and stretch out the foldable reticulated polylactic acid stent 4 and attach to the inner wall of the affected area, and then the liquid is drawn out, and when the elastic balloon 2 is shrunk, the tubular body 1 is withdrawn.

The degradable foldable biological amniotic membrane composite repair stent is made by the following method: a foldable reticulated polylactic acid stent 4 is woven from a filamentous degradable polylactic acid material with a plurality of micropores, and foldable reticulated polylactic acid stent 4 is uniformly sprayed with compound amniotic membrane gel, the elastic balloon 2 is placed in the lumen of the foldable reticulated polylactic acid stent 4, and then sheet-shaped biological amniotic membrane 5 is wrapped on the outer surface of the foldable reticulated polylactic acid stent 4. The biological amniotic membrane 5 can be fixed with the foldable reticulated polylactic acid stent 4 with medical adhesive, and then put into a squeeze machine for compression. The compression process includes two stages. In the first stage, adjust the pressure of the squeeze machine to 0.5 MPa and hold 15 min, and in the second stage, adjust the squeeze machine to 1 MPa and hold 5 min; after compression, package and sterilize to obtain a degradable foldable biological amniotic membrane composite repair stent.

EXAMPLE 3

A degradable foldable biological amniotic membrane composite repair stent, comprising a tubular body 1 with an axially extending through hole, the front end of the tubular body 1 is provided with an elastic balloon 2, and the end of the tubular body 1 is connected to a one-way valve 3 which seals the through hole here, the elastic balloon 2 is arranged in the lumen of a foldable reticulated polylactic acid stent 4, sheet-like polylactic acid and sheet-like amniotic membrane are laminated and wound on the outer surface of the elastic balloon 2, there are a plurality of micropores on the sheet-like polylactic acid and the plurality of micropores are filled with biological amniotic membranes; in the initial state, the elastic balloon 2, the sheet-like polylactic acid, and the sheet-like amniotic membrane are compressed into a tight state; in the use state, the elastic balloon 2 is injected with sterile gas or liquid to expand to adapt to the shape of the affected area, and stretch out the sheet-like polylactic acid and the sheet-like amniotic membrane and attach to the inner wall of the affected area, and then the sterile gas or liquid is drawn out, and when the elastic balloon 2 is shrunk, the tubular body 1 is withdrawn. The sheet-like polylactic acid has a limit position after being stretched by the elastic balloon 2, and the sheet-like polylactic acid is provided with a locking mechanism to maintain the limit position, the sheet-like polylactic acid is made of polylactic acid material by 3D printing polylactic acid sheet with meshes.

The degradable foldable biological amniotic membrane composite repair stent is made by the following method: a degradable polylactic acid material is made into polylactic acid sheet with meshes by 3D printing, and a plurality of micropores are engraved on the polylactic acid sheet with meshes by laser engraving, and then a layer of amniotic membrane fragments is evenly spread on the polylactic acid sheet with meshes. Put it in the press, control the pressure at 1 MPa, and press for 10 minutes; then laminate and wind the polylactic acid sheet with meshes and sheet-like amniotic membrane on the outer surface of the elastic balloon, then put into a squeeze machine for compression. The compression process includes two stages. In the first stage, adjust the pressure of the squeeze machine to 1 MPa and hold 10 min, and in the second stage, adjust the squeeze machine to 2 MPa and hold 3 min; after compression, package and sterilize to obtain a degradable foldable biological amniotic membrane composite repair stent.

The foregoing descriptions are only preferred embodiments of the present invention and are not intended to limit the present invention. Any changes or substitutions that can be easily conceived by those skilled in the art within the technical scope disclosed herein shall fall into the scope of protection of the present invention. Therefore, the scope of protection of the present invention shall be subject to the protection scope defined by the claims.

The invention claimed is:

1. A degradable foldable biological amniotic membrane composite repair stent, comprising:
   a tubular body that defines an axially extending through hole, and comprises a front end that is provided with an elastic balloon, and an opposite rear end connected to a one-way valve which seals the through hole; and
   a foldable reticulated polylactic acid stent having an outer surface that is coated with a biological amniotic membrane, a mesh defining a plurality of micropores that are filled with biological amniotic membrane powder, and the biological amniotic membrane powder is independent of the biological amniotic membrane;
   wherein the elastic balloon is arranged in a lumen of the foldable reticulated polylactic acid stent, in an initial state, the elastic balloon, the foldable reticulated polylactic acid stent, and the biological amniotic membrane are compressed into a tight state; in an use state, the elastic balloon configured to expand to adapt to a shape of a body cavity of an affected area and stretch out the foldable reticulated polylactic acid stent after sterile gas or liquid is injected into the elastic balloon, and the elastic balloon is configured to be shrunk after the sterile gas or liquid is drawn out, thereby allowing the tubular body to be withdrawn.

2. The degradable foldable biological amniotic membrane composite repair stent according to claim 1, wherein the foldable reticulated polylactic acid stent is woven from filamentous polylactic acid.

3. The degradable foldable biological amniotic membrane composite repair stent according to claim 1, wherein the foldable reticulated polylactic acid stent is made of polylactic acid material by laser engraving.

4. The degradable foldable biological amniotic membrane composite repair stent according to claim 1, wherein the foldable reticulated polylactic acid stent is made of polylactic acid material by 3D printing.

5. A degradable foldable biological amniotic membrane composite repair stent, comprising:
   a tubular body that defines an axially extending through hole, and comprises a front end that is provided with an elastic balloon, and an opposite second end connected to a one-way valve which seals the through hole;
   a sheet-like polylactic acid defining a plurality of micropores that are filled with biological amniotic membrane powder; and
   a sheet-like amniotic membrane, wherein the sheet-like polyactic acid and the sheet-like amniotic membrane are laminated and wound on an outer surface of the elastic balloon, and the biological amniotic membrane powder is independent of the sheet-like amniotic membrane;
   wherein in an initial state, the elastic balloon, the sheet-like polylactic acid, and the sheet-like amniotic membrane are compressed into a tight state; in an use state, the elastic balloon is configured to expand to adapt to a shape of a body cavity of an affected area, and stretch out the sheet-like polylactic acid and the sheet-like amniotic membrane after sterile gas or liquid is injected into the elastic balloon, and the the elastic balloon is configured to be shrunk after the sterile gas or liquid is drawn out, thereby allowing the tubular body to be withdrawn.

6. The degradable foldable biological amniotic membrane composite repair stent according to claim 5, wherein the sheet-like polylactic acid comprises a mesh, and the plurality of micropores are defined in the mesh.

* * * * *